(12) United States Patent
Dahm (10) Patent No.: US 7,323,304 B2
(45) Date of Patent: Jan. 29, 2008

(54) METHOD FOR THE IMMUNOCYTOLOGICAL OR MOLECULAR DETECTION OF DISSEMINATED TUMOR CELLS FROM A BODY FLUID AND KIT THAT IS SUITABLE THEREFOR

(75) Inventor: Michael W. Dahm, Munich (DE)

(73) Assignee: Hexal Gentech ForschungsGmbH, Holzkirchen (DE)

( * ) Notice: Subject to any disclaimer, the term of this patent is extended or adjusted under 35 U.S.C. 154(b) by 250 days.

(21) Appl. No.: 10/524,544

(22) PCT Filed: Aug. 7, 2003

(86) PCT No.: PCT/EP03/08796

§ 371 (c)(1),
(2), (4) Date: Feb. 14, 2005

(87) PCT Pub. No.: WO2004/023110

PCT Pub. Date: Mar. 18, 2004

(65) Prior Publication Data

US 2006/0057650 A1    Mar. 16, 2006

(30) Foreign Application Priority Data

Aug. 14, 2002 (DE) ............................... 102 37 296

(51) Int. Cl.
*C12Q 1/68* (2006.01)
*A01N 1/02* (2006.01)

(52) U.S. Cl. .............................................. 435/6; 435/2

(58) Field of Classification Search .................... None
See application file for complete search history.

(56) References Cited

U.S. PATENT DOCUMENTS

| 5,840,502 | A | 11/1998 | Van Vlasselaer |
| 6,821,726 | B1 * | 11/2004 | Dahm et al. .................. 435/6 |
| 7,211,433 | B1 | 5/2007 | Dahm |

FOREIGN PATENT DOCUMENTS

| WO | WO 96/17080 | * | 6/1996 |
| WO | WO 98/17080 A1 | | 6/1996 |
| WO | WO 97/21488 | * | 6/1997 |
| WO | WO 97/21488 A1 | | 6/1997 |

OTHER PUBLICATIONS

Traweek, S.T., Liu, J., and Battifora, H. Keratin gene expression in non-epithelial tissues. 1993. American Journal of Pathology, vol. 142 No. 4, pp. 1111-1118.*
Slade, M.J. and Coombes, R.C. The clinical significance of disseminated tumor cells in breast cancer. 2007. Nature Clinical Practice Oncology. vol. 4 No. 1; pp. 30-41.*
Goetz, Alexander, "Mit OncoQuick den Metastasen auf der Spur", BIOforum forschung und entwicklung, p. 394, 2001, vol. 24, XP-002261836, GIT VERLAG GmbH, Darmstadt, Germany.
English language translation of Abstract paragraph for Goetz article "Mit OncoQuick den Metastasen auf der Spur", BIOforum forschung und entwicklung, 24 (201) 394, 2001.
Hexal Gentech Forschungs-GmbH: Oncoquick-TM Gebrauchsanleitung, Online!; greiner bio-one, oncoQuick Instruction Manual, http://www.hexal-gentech.de/products/man_d.pdf, XP002261835, Feb. 12, 2007.
Alexander W. Goetz et al., "Enrichment of disseminated breast cancer cells from human peripheral blood by advanced density gradient centrifugation", Proceedings of the American Association for Cancer Research Annual Meeting, Mar. 2002, p. 733, vol. 43, XP002261837.
J. Bischoff et al., "Detection of disseminated tumor cells in bone marrow and peripheral blood of patients with metastatic breast cancer", Annual Meeting of the American Society of Clinical Oncology, May 2002, XP002261838.
R. Rosenberg et al., "Comparison of Two Density Gradient Centrifugation Systems for the Enrichment of Disseminated Tumor Cells in Blood", Cytometry, Dec. 1, 2002, pp. 150-158, vol. 49, No. 4.

* cited by examiner

*Primary Examiner*—Larry R. Helms
*Assistant Examiner*—Anne M. Gussow
(74) *Attorney, Agent, or Firm*—Arent Fox, LLP (57) ABSTRACT

The invention relates to a method for enriching tumor cells from a body fluid, in which a cell separation medium of a specific density is overlaid with the body fluid and it is subsequently determined whether the enriched cells express an epithelial marker, for example a cytokeratin. A kit suitable for this method is likewise provided.

7 Claims, 3 Drawing Sheets

Figure 1

Figure 2 a. Cytospin after Ficoll® centrifugation (40x magnification)

b. Cytospin after OncoQuick® centrifugation (40x magnification)

Figure 3 a. CK-20 RT-PCR after Ficoll® centrifugation 370 bp b. CK-20 RT-PCR after OncoQuick® centrifugation 370 bp

METHOD FOR THE IMMUNOCYTOLOGICAL OR MOLECULAR DETECTION OF DISSEMINATED TUMOR CELLS FROM A BODY FLUID AND KIT THAT IS SUITABLE THEREFOR

This application is a 371 of PCT/EP2003/008796 filed Aug. 7, 2003, which is hereby incorporated by reference.

The invention relates to methods for detecting tumor cells from a body fluid, and kits suitable therefor.

Virtually all solid malignant tumors have the potential to form metastases. The process of metastasis comprises the dissemination of malignant cells as micro-metastases, usually via the blood or lymph to remote organs, and the development of autonomous secondary tumors. The extent of the filiarization determines the prognosis of a neoplastic disease.

The requirements of tumor prevention or aftercare programs are to diagnose primary tumors or recurrences early, or metastases even before they become clinically manifest. This aim cannot yet be satisfactorily met with the available instrumental techniques. Detection of circulating or disseminated tumor cells for example in peripheral blood would make it possible to initiate a possibly curative immunomodulating therapy or polychemotherapy at an early date, i.e. even before the appearance of a tumor which is noticed clinically. Quantification of tumor cells in peripheral blood before and after the therapy represents an important control in such cases.

A promising approach to detecting and quantifying disseminated tumor cells consists of determining epithelial markers such as cytokeratins in a body fluid. For example, Racila et al. describe, in Proc Natl Acad Sci USA (1998) 95: 4589, an assay with which disseminated epithelial tumor cells can be detected by means of monoclonal antibodies against cytokeratin in peripheral blood. In addition, commercial molecular kit systems permitting, for example, determination of cytokeratin 20 expression in a sample by means of PCR already exist (Roche LightCycler-CK20 Quantification Kit).

Cytokeratins belong to the family of filamentous proteins which are involved in the structure of the cytoskeleton of epithelial cells (Moll et al. in Cell (1982) 31: 11). Since epithelial cells normally do not occur in peripheral blood, it is postulated that cytokeratin expression in blood is a surrogate marker for the presence of disseminated tumor cells.

However, it is possible in peripheral blood for not only tumor cells but also other blood cells such as polymorphonuclear leukocytes, specifically granulocytes, to express epithelial markers such as cytokeratins (Jung et al. Br J Cancer (1999) 81: 870). Because of this fact it is necessary before detecting an epithelial marker, such as, for example, cytokeratin expression as surrogate marker for disseminated tumor cells in blood, to carry out a separation of these non-tumor cells which express the epithelial marker, such as, for example, express cytokeratin, from the tumor cells which express an epithelial marker such as, for example, cytokeratin.

In the 1960s and 70s, when methods such as, for example, FACS or MACS were not yet available, tumor cells were separated from hematopoietic cells on the basis of their different density (J. A. Fleming et al., J. clin. Path. (1967), 20, 145). According to these data, tumor cells have a specific density of 1.040-1.080, whereas the density of erythrocytes is higher and that of lymphocytes is similar. Polymorphonuclear leukocytes by contrast have a specific density in the range of 1.060-1.080 and thus overlap with the specific density of tumor cells. Complete removal of the likewise cytokeratin-positive granulocytes from the tumor cells via the differences in density thereof ought therefore to be impossible. Thus, the use of a standard solution for isolating lymphocytes, such as, for example, Histoprep® (Sigma) with a density of 1.077 g/ml, also showed that granulocytes from healthy blood donors with a density of up to 1.077 g/ml are cytokeratin-positive (Jung et al. Br J Cancer (1999) 81: 870).

One object of the present invention is thus to provide an advantageous method for detecting tumor cells from a body fluid.

It has now surprisingly been found that it is possible to separate cytokeratin-expressing non-tumor cells from cytokeratin-expressing tumor cells by OncoQuick®, a method described in WO 99/40221 and WO 00/46585. OncoQuick® (Greiner Bio One, Frickenhausen, Germany) uses as discontinuous gradient a cell separation medium which has a higher density than the body fluid to be investigated and is overlaid with the body fluid. Centrifugation fractionates the cells according to their specific cell density, and they can be removed in individual fractions. It has surprisingly been found that cytokeratin-positive and cytokeratin-negative blood cells can be separated from one another through the specific level of density of the cell separation medium, with the enriched tumor cells being present after the centrifugation in the same fraction as the cytokeratin-negative blood cells, so that subsequent detection of cytokeratin expression in this fraction can be attributed without doubt to tumor cells being present.

The present invention therefore relates to a method for detecting disseminated tumor cells from a body fluid, in which (a) tumor cells are enriched by a cell separation medium which has a density in the range from 1.055 to 1.065 g/ml being overlaid with the body fluid and being centrifuged; and (b) it is determined whether the enriched cells express an epithelial marker such as, for example, a cytokeratin.

Expression of an epithelial marker can then be regarded as surrogate for the presence of disseminated tumor cells.

The body fluid from which cytokeratin-positive tumor cells are to be enriched may be human or animal body fluids or a dispersion of cellular tissue. Examples in this connection are blood, especially peripheral blood such as venous or arterial blood, portal blood or blood from a central venous catheter (CVC), lymph, urine, exudates, transudates, spinal fluid, seminal fluid, saliva, fluids from natural or unnatural body cavities, bone marrow and dispersed body tissue. The fluids from natural body cavities may be for example serous fluids such as peritoneal and pleural fluids, and the fluids from unnatural body cavities may be for example fluids from cysts.

Preferred body fluids are blood, bone marrow, lymph, serous fluids from body cavities, and urine, with particular preference for blood and urine. Urine is particularly suitable for enriching cells from bladder tumors.

The most preferred body fluid is, however, peripheral blood, which is advantageously taken in an anticoagulant substance and diluted with a diluent before the overlaying of the cell separation medium. Examples of anticoagulant substances which can be employed are EDTA or citrate and heparin or CPD (citrate, phosphate, dextrose) or comparable substances. Venous or arterial blood is suitable as peripheral blood.

Preferred tumor cells are tumor cells derived from a solid tumor, in particular from tumors of epithelial origin and particularly preferably tumor cells which express a cytokeratin. Examples of epithelial tumors are carcinomas such as carcinomas of the breast, of the prostate or gastrointestinal tumors, but without being restricted thereto.

The body fluid to be investigated is taken or collected, as described in WO 99/40221 and WO 00/46585, in accordance with conventional standard protocols. Depending on the nature of the body fluid, it is then either firstly diluted with a diluent, preferably a buffer, or layered directly, undiluted, over the cell separation medium in a closable centrifugation vessel. Alternatively, the body fluid can previously be centrifuged at, for example, 1 000×g for about 10 minutes and, after resuspension of the cells in a buffer, layered over the cell separation medium. The buffer which is preferably used is Dulbecco's PBS.

The centrifugation is advantageously carried out at about 500 to 2 000×g, preferably at about 1 000×g, for about 10 to 30 minutes, preferably for 20-30 minutes. The temperature during the centrifugation is preferably about 4° C. The effect of this that catalytic activity of proteases, DNAses and RNAses is minimized.

The cell separation medium which can be used is in principle any suitable fluid of desired density. The density is in the range from 1.055 to 1.065 g/ml, preferably in the range from 1.059 to 1.062 g/ml and is most preferably 1.060±0.0005 g/ml. The density in a particular embodiment is less than 1.065 g/ml, i.e. from 1.055 to <1.065 g/ml. The cell separation medium ought not to react with the body fluid or the cells present therein. It is advantageously possible for example to use Ficoll® (high mass polysaccharide that dissolves in aqueous solutions) or Percoll®, (medium containing colloidal silica particles coated with polyvinylpyrrolidone) or a Percoll- or Ficoll®-like medium, with the solutions in each case being brought to the desired density in accordance with the manufacturer's instructions. The density of the cell separation medium is advantageously adjusted with the aid of density meter (DMA 4500, Anton Paar, Austria) at the appropriate working temperature of 4° C. The procedure described in WO 00/46585 for preparing a solution of desired density is incorporated in the disclosure of this application by reference. The cell separation medium may comprise a dye which makes the cell separation medium distinguishable in color from the overlying body fluid, and thus simplifies location of the interphase.

In order to ensure that the operations take place as simply as possible, it is possible in a preferred embodiment of the method of the invention to carry out the centrifugation, as described in WO 99/40221 and WO 00/46585, in a closable vessel which is divided by a barrier, a filter or a sieve, called porous barrier or barrier hereinafter, into an upper and a lower compartment, the cell separation medium being introduced into the lower compartment, and the body fluid being put in the upper compartment.

The barrier preferably has a porous nature which allows fluids and the corpuscular constituents of the blood, such as the cells of the red and white blood system, which have a higher density than the introduced cell separation medium, to be able to pass unhindered through the porous barrier during the centrifugation. The result of this is that the cell separation medium is forced during the centrifugation through the porous membrane into the upper compartment, and the tumor cells and platelets, which have a lower density than the introduced cell separation medium, come to rest at a level above the barrier.

The porous barrier may consist of any suitable material. Suitable examples are plastics, metal, ceramic or a mixture or special alloy of these materials. However, it is also possible to employ any other natural or artificial material which is suitable. In a preferred embodiment, the porous barrier consists of a hydrophobic material or is coated with a hydrophobic material.

As an alternative to the barrier as described in WO 99/40221 and WO 00/46585 in a centrifugation vessel it is also possible to employ a flap which, analogous to the barrier, divides the centrifugation vessel into an upper and lower compartment.

This flap has a nature which allows it to be tightly closed before and after the centrifugation and to be opened only during the centrifugation due to the centrifugal force. During the centrifugation, with the flap open, the liquids in the lower and upper compartment come together. The result of this is that the cells of the red and white blood system, which have a higher density than the introduced cell separation medium, enter the lower compartment and displace the cell separation medium into the upper compartment. The effect of this is that the tumor cells, which have a lower density than the introduced cell separation medium, come to rest at a level above the flap.

The porous barrier, the filter, the sieve or the flap may have a thickness of 0.5-10 mm, preferably of 1-5 mm. The porous barrier, the filter, the sieve or the flap may have a pore size of 20-100 μm, preferably 20-30 μm.

It is possible with the aid of the porous barrier or flap to charge the centrifugation vessel with the body fluid to be investigated, without it mixing with the underlying cell separation medium, and thus possibly impairing or rendering impossible the enrichment. After the centrifugation, the tumor cells present in the body fluid are located in the interphase of the upper compartment of the centrifugation vessel. The interphase is formed between the separation medium and the residual fluid of a body fluid or a cell suspension and comprises the enriched tumor cells. When blood is used as body fluid for example, this residual fluid is plasma, a plasma/PBS or plasma/buffer mixture which comprises the plasma proteins. About 80% of the fluid above the interphase can then be cautiously aspirated off and discarded.

The remaining supernatant above the barrier or flap, in which the tumor cells are located, can subsequently be collected and, for example, transferred into a fresh centrifugation vessel (preferably made of optionally siliconized plastic and having the same volumetric capacity as the centrifugation vessel used previously). The porous barrier or the closed flap prevents the cells in the upper and the lower compartment becoming mixed on removal of the remaining supernatant.

The upper compartment of the centrifugation vessel is then advantageously washed, for example twice as described in WO 99/40221 and WO 00/46585, with a buffer, and the latter is likewise transferred into the fresh centrifugation vessel. After a further centrifugation, for example at 1 000×g for about 10 minutes at a temperature of about 4° C., the collected cells can then be passed on to the tumor cell detection methods. A suitable washing buffer is, for example, Dulbecco's PBS (3.9 mM EDTA, pH 8.0; without Ca/Mg).

Further washing buffers are disclosed in WO 99/40221 and WO 00/46585.

However, if a centrifugation vessel with a porous barrier or flap is used, as described in WO 99/40221 and WO 00/46585, removal of the supernatant residual fluid above the interphase is followed by removal not just of the interphase but of the entire remaining fluid above the porous barrier, not because further cells are also located between the interphase and porous barrier or flap, but because the cells contained in the cell ring may easily become mixed through the removal. In order not to lose any cells from the upper compartment, it is advantageously washed twice more with a buffer (e.g. PBS with 0.1%-10% BSA).

It is possible with the method of the invention for disseminated tumor cells and, in particular, disseminated tumor cells from epithelial tumors to be separated completely, because of their different density, from the corpuscular constituents of body fluids such as, for example, the cells of the red and white blood system, and be concentrated, and for example for the cytokeratin expression of the enriched tumor cells to be detected by means of immunocytological or molecular biological tumor cell detection methods. For the purposes of this application, a cell expresses a particular epithelial marker such as, for example, a particular cytokeratin when the cell comprises the protein of the epithelial marker such as, for example, a cytokeratin protein, or the mRNA coding therefor. Preferred epithelial markers are cytokeratins. Cytokeratins which can be detected according to the invention are cytokeratins 1-20, preferably 1, 4-8, 10-11, 13-20, particularly preferably a combination of cytokeratins 1, 4-8, 10-11, 13-20. The most preferred combination for the immunocytochemical detection are antibodies for cytokeratin 8, 18, 19 and 20. The preferred cytokeratins for the molecular detection are cytokeratin 18, 19 and 20, with most preference for cytokeratin 20. Examples of further epithelial markers are prostate specific antigen (PSA, Israeli et al., 1994, Cancer Res 54, 6306-6310), the human melanoma antigen (MAGE)-encoding gene family (De Plaen et al., 1994, Immunogenetics 40, 360-369), Hasegawa et al., 1998, Pathol Lab Med 122, 551-554), breast-specific antigens such as MAS-385, SB-6 (Ross et al., 1993, Blood 82, 2605-2610), MUC-1 (Brugger et al., 1999, J Clin Oncol 17, 1535-1544) and GA733-2 (Zhong et al., 1999, Tumordiagn. u. Ther. 20, 39-44), adhesion molecules such as TFS-2, EPCAM (Racila et al., 1998, Proc Natl Acad Sci USA 95, 4589-4594) or CEACAM1 (Thies et al., 2002, J Clin Oncol 20, 2530-2536), receptor molecules such as estrogen-progesterone receptors (Bitran et al., 1992, Dis Mon 38, 213-260), carcinoembrionic antigen (CEA, Liefers et al., 1998, N Engl J Med 339, 223-228), PRL-3 protein, a tyrosine phosphatase (Saha et al. 2001, Science 294, 1343-1346) or maspin, a protein from the serpin family (Sabbatini et al., 2000, J Clin Oncol 18, 1914-1920) without being restricted thereto.

The methods for detecting expression of epithelial markers, in particular cytokeratin expression, encompass the whole range of conventional diagnostic methods. Examples thereof are microscopic, immuno-cytological/immunocytochemical, biochemical and/or molecular biological methods. It is possible for example to detect the expression of epithelial markers, in particular cytokeratin expression, after enrichment directly or after cell culture and expansion of the tumor cells by morphological, immunocytological/immunocytochemical, biochemical and/or molecular biological methods. It is possible in this connection for cell constituents of epithelial markers, especially cytokeratin-specific cell constituents, to be detected, e.g. the protein of an epithelial marker such as, for example, the cytokeratin protein itself, specific sections of chromosomes and even nucleic acid sequences such as DNA, RNA and cDNA.

In one embodiment, determination of whether the enriched cells express an epithelial marker such as, for example, a cytokeratin includes reverse transcription of mRNA from the enriched cells, and carrying out a PCR with at least one primer specific for the epithelial marker, e.g. a cytokeratin-specific primer. In another embodiment, the enriched cells are brought into contact with a monoclonal antibody which is specific for an epithelial antigen such as, for example, a particular cytokeratin, and subsequently antibody bound to the cells is detected. These methods can be carried out in single or combination analysis. In a preferred embodiment there is use of antibodies which, as in the case of the murine monoclonal antibody A45-B/B3 (Micromet, Germany), recognize a common epitope of various cytokeratins (8, 18 and 19). It is also possible to combine antibodies such as, for example, the antibody A45-B/B3 together with a cytokeratin 20 antibody. In the case of a molecular analysis it is possible for example to carry out PCR investigations with two specific primers or pairs of primers which are specific for two different epithelial markers. An alternative possibility is to repeat the abovementioned investigations also with another antibody or with another primer or pair of primers which are specific for a further epithelial marker. In a preferred embodiment there is use of custom-made microarrays with which different epithelial markers can be detected in combination with tumor-specific markers such as, for example, telomerase, in one investigation step.

Examples of direct detection methods are, inter alia, all types of microscopy including staining of cell constituents. One example of direct staining is staining by specific antibodies which are directed against cytokeratins and to which labeling signals such as, for example, fluorescent dyes are coupled. Detection methods are inter alia flow cytometry or FACS (fluorescence activated cell sorting), ELISA and Western blotting. Further methods for detecting epithelial markers such as, for example, cytokeratins are inter alia nucleic acid detection methods with the aid of labeled probes, e.g. FISH, in situ hybridization, Northern, South-Western and Southern blotting or differential display, and inter alia nucleic acid amplification methods, inter alia PCR, RT-PCR, in situ RT-PCR, real-time PCT and NASBA. The reagents which can be used in these cases are those which detect a plurality of epithelial markers such as, for example, cytokeratins, i.e. are specific for a group of epithelial markers such as, for example, cytokeratins. However, it is also possible to use reagents which specifically detect only a particular epithelial marker such as, for example, only a particular cytokeratin, e.g. a monoclonal anti-CK-20 antibody or CK-20-specific primers for specific RT-PCR detection of CK-20. Anti-cytokeratin antibodies are commercially available or can be prepared by methods known per se. Primers can be derived from the cDNA sequences of the various cytokeratins. The cDNA sequence of CK-20 is deposited in the NCBI database http://www.ncbi.nlm.nih-.gov under the Accession No. BC031559 (*Homo sapiens*, cytokeratin 20, clone MGC:35423, IMAGE:5189289, mRNA, complete cds).

The subsequent detection methods can be employed in the following areas:

Detection of the expression of epithelial markers, such as, for example, that of cytokeratin expression in the enriched cells, can be employed directly as tumor marker. In staging investigations it is possible to correlate the number of detected disseminated tumor cells with the clinical picture, and establish an individual tumor staging. After removal of the primary tumor, the patient can undergo regular checks for recurrence and be immediately treated if there is a positive finding. Further possible uses are the detection of residual tumor cells in the bone marrow of patients who must undergo high-dose radiotherapy, or of disseminated tumor cells within the framework of new therapeutic approaches, and ex vivo and in vivo gene therapeutic approaches.

Particular value is ascribed to the method within the framework of tumor screening investigations because longer survival rates are to be expected with considerably earlier diagnosis and immediate therapy. Further applications are in the production of tumor vaccines and in gene therapy.

The present invention thus also relates to a method for detecting tumor cells in a body fluid, in which the tumor cells are enriched as described above from a body fluid and, preferably simultaneously, unwanted cells are depleted to a high degree, and disseminated tumor cells expressing one or more epithelial markers, such as, for example, cytokeratin-expressing tumor cells, are detected by means of immuno-cytological or molecular biological techniques.

The present invention further relates to a kit for the enrichment of disseminated tumor cells from a body fluid, said kit being suitable for carrying out the method of the invention. For this purpose, the kit includes the cell separation medium disclosed in WO 99/40221 and WO 00/46585, and means for detecting the expression of epithelial markers such as, for example, of a cytokeratin and, where appropriate, a centrifugation vessel and/or washing buffer in optionally concentrated form for washing the enriched cells. The preferred embodiments of the components of the kit correspond to those described for the method of the invention.

In order to facilitate routine work with the kit, the centrifugation vessel may have a porous barrier or flap which divides the centrifugation vessel into an upper and a lower compartment. The advantageous embodiments of the centrifugation vessel correspond to those described above for the method of the invention.

The present invention further relates to an immuno-cytological kit for detecting tumor cells enriched from a body fluid, which is suitable for carrying out the method of invention. For this purpose, the kit includes specific monoclonal antibodies with which tumor cells expressing epithelial markers, such as, for example, expressing cytokeratin, can be detected immuno-cytologically. The antibodies may be those which recognize a plurality of cytokeratins or those which recognize only one cytokeratin.

The present invention further relates to a molecular biological kit for detecting tumor cells enriched from a body fluid, which is suitable for carrying out the method of the invention. For this purpose, the kit includes specific primers and, where appropriate, enzymes with which tumor cells expressing epithelial markers, such as, for example, expressing cytokeratin, can be detected by means of reverse transcriptase polymerase chain reaction (RT-PCR) or by means of real-time polymerase chain reaction (PCR). The primers preferably amplify specifically only one cDNA of an epithelial marker or only one cytokeratin cDNA, and the primers particularly preferably amplify specifically only CK-18 cDNA, CK-19 cDNA and/or CK-20 cDNA, and the most preferred primers amplify specifically only CK-20 cDNA.

The method of the invention has the advantage that epithelial marker-positive cells such as, for example, cytokeratin-positive non-tumor cells can be separated simply and reliably from the tumor cells to be enriched, so that no false-positive results due to epithelial marker-positive cells such as, for example, cytokeratin-positive non-tumor cells are obtained in subsequent detection methods. Thus, non-tumor cells which express at least one of cytokeratins 1-20 can be separated from tumor cells which express at least one of cytokeratins 1-20. In particular, CK-20-positive non-tumor cells can be separated from CK-20-positive tumor cells. In addition, only a few working steps are necessary for the enrichment and isolation of tumor cells from body fluids, so that the processing of relatively large amounts of sample material becomes possible thereby. The costs of the necessary materials are significantly lower for example compared with the use of specific antibodies and the subsequent separation by means of suitable apparatuses.

The unlikely event of obtaining a false-positive result can be additionally precluded by fixing a particular value above which a result is assessed as positive (cut-off). For example, a signal after RT-PCR, in particular after real-time PCR, with a spiked sample having 2-10 cells/ml (e.g. having 2, 4, 6, 8 or 10 cells/ml), can be fixed as minimum signal for a positive detection. Real-time PCR makes it possible to determine the copy number of the amplicon by means of quantification software (Roche). If the value of the amplicon is above a previously established minimum copy number, the result can be assessed as positive. A similar procedure is possible with custom-made microarrays, where the intensity of the signal found must be above a previously determined intensity level.

Figure 1:
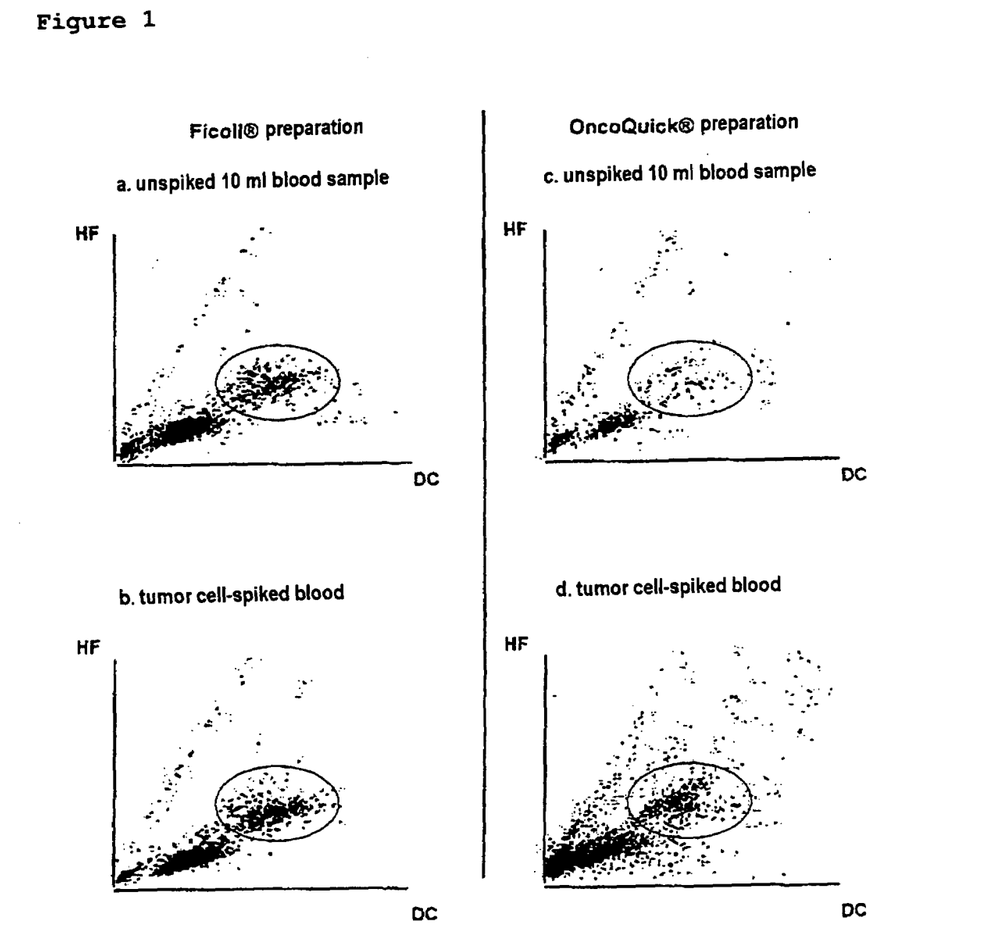

FIG. 1 shows a hematological analysis (Sysmex SE-9000) of 10 ml of peripheral blood from healthy subjects which has been been purified with Ficoll® (a, b) or OncoQuick® (c,d). a) and c) are unspiked samples, b) and d) are samples spiked with tumor cells. The unspiked blood samples contained $1.8\times10^7$ blood cells after Ficoll® enrichment (a) and $9.5\times10^4$ after OncoQuick® enrichment (c). After the samples had been spiked with $2.7\times10^6$ tumor cells, the tumor cell fraction (mainly in the region identified by the ellipse) forms the main fraction after OncoQuick® enrichment (d), whereas the tumor cells are enriched after Ficoll® enrichment (b) with a large number of MNCs. HF=high frequency, DC=direct current).

Figure 2:
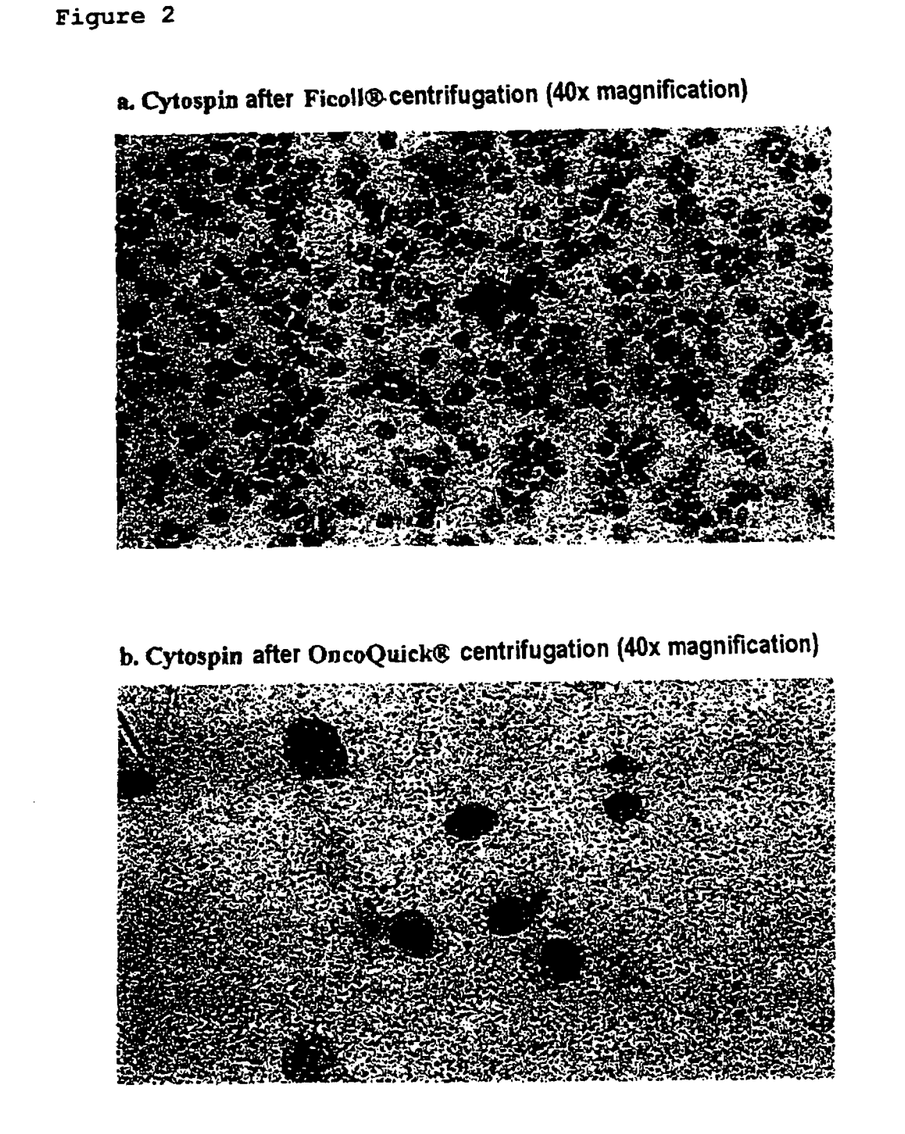

FIG. 2 shows immunocytological detection using the pancytokeratin antibody A45-B/B3 of 10 ml of peripheral blood from healthy subjects, with 100 spiked tumor cells after enrichment with Ficoll® (a) or OncoQuick® (b). After enrichment using OncoQuick®, the complete enriched cell fraction was centrifuged with an elevated tumor cell density on 1-2 slides, compared with 50 slides after Ficoll® enrichment.

Figure 3:
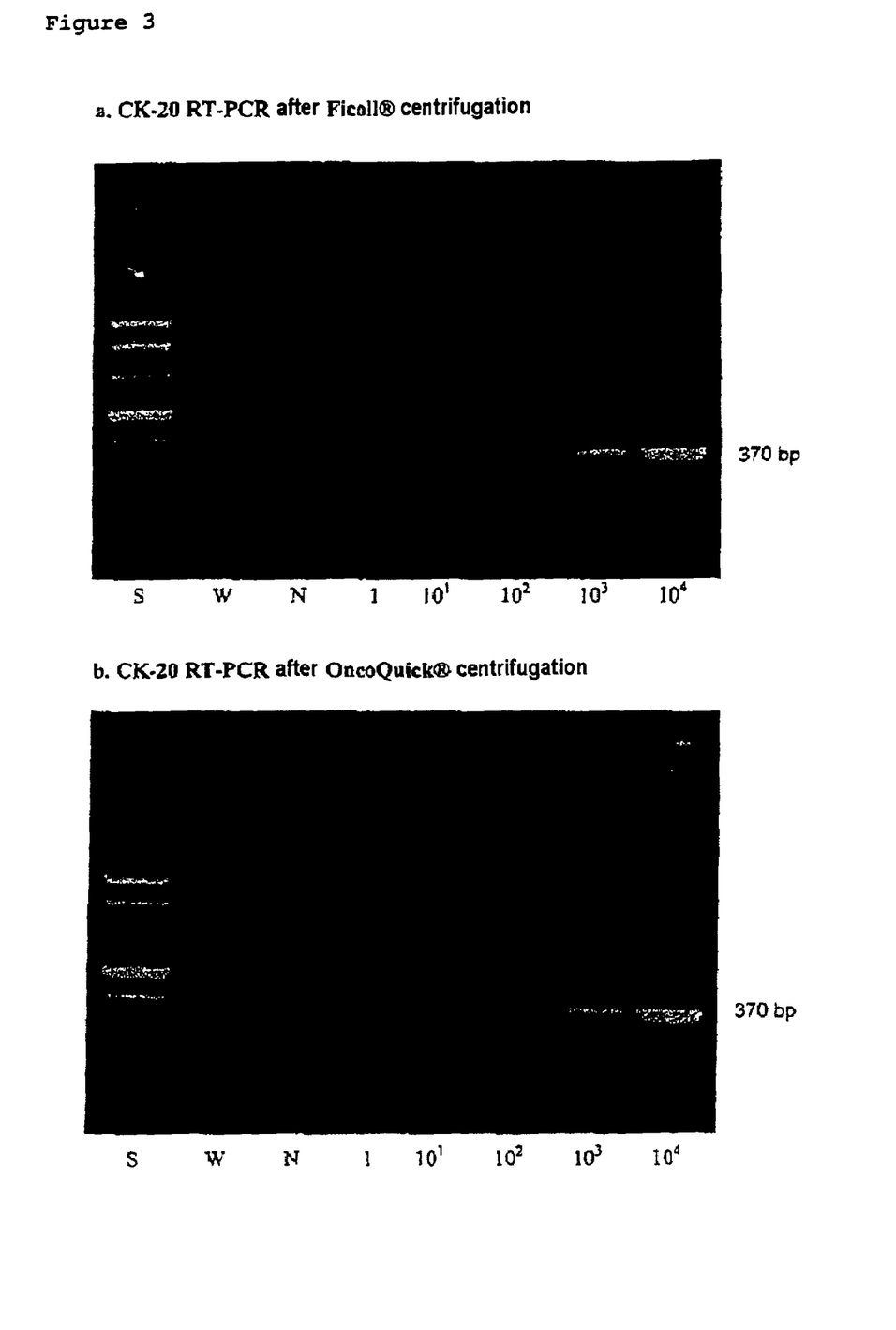

FIG. 3 shows a CK-20 RT-PCT of blood samples spiked with 1 to $10^4$ tumor cells after enrichment with Ficoll® (a) or OncoQuick® (b). Whereas 10 tumor cells can be detected in 30 ml of blood with OncoQuick®, preparations with Ficoll® are limited to an amount of only 10 ml of blood. Water (W), negative controls (N) and DNA length standard VII (Roche, Germany) (S).

The following examples explain the invention in more detail.

EXAMPLE 1

This experiment was carried out in order to find whether CK20 mRNA-expressing non-tumor cells can be successfully depleted by OncoQuick®.

OncoQuick® is a commercially available cell separation system which displays the following features: it includes a 50 ml centrifugation vessel which is divided by a porous barrier into 2 compartments. The lower compartment contains the cell separation medium with a density in the range according to the invention. The body fluid to be investigated can be introduced into the upper compartment.

The experiment was carried out on a group of 70 healthy subjects, and the evaluation was undertaken with the most sensitive amplification method, real-time PCR. A total amount of 30 ml of peripheral blood was taken from each of the total of 70 healthy subjects and divided into two equal aliquots of 15 ml. One aliquot was in each case purified using Ficoll® (Leucosep® (centrifugation vessel containing a porous barrier) Greiner Bio One), and the other aliquot was purified using OncoQuick® (Greiner Bio One) as stated by the manufacturer. 50 ml Leucosep® centrifugation vessels contain, like OncoQuick®, a porous barrier which divides the tube into an upper and into a lower compartment. 15 ml of Ficoll® are placed in the lower compartment. 10 ml of blood were introduced into the centrifugation vessel and centrifuged at 1000 g for 10 minutes at room temperature. 10 ml of blood were introduced analogously into a precooled OncoQuick® centrifugation vessel and centrifuged at 1600 g for 20 minutes at 4° C. The entire upper compartment was removed and transferred into a fresh 50 ml centrifugation vessel. The collected cells were washed once with PBS (Boehringer, Germany) at 500 g for 15 minutes (Ficoll®) and with the OncoQuick® washing buffer at 200 g for 12 minutes (OncoQuick®) at 4° C. The washed cells were then collected and the total RNA was extracted using the High Pure® RNA Isolation Kit (Roche, Germany) as stated by the manufacturer. The RNA was then eluted in 70 µl. 10 µl of the eluted RNA were then transferred into a 20 µl reverse transcriptase reaction of the LightCycler® (real time PCR system) CK20 quantification kit (Roche, Germany), and subsequently 5 µl were employed in the real-time PCR as stated by the manufacturer. Evaluation of the results showed that 8 individual samples were CK-20-positive in the samples enriched with Ficoll®. By comparison therewith, the samples purified with OncoQuick® were negative.

EXAMPLE 2

1. Material and Methods

Density Gradient Centrifugation of the Blood Samples

For all the experiments, peripheral venous blood was taken from tumor-free patients using EDTA-coated 10 ml Monovette® (a blood collection tube) (Sarstedt, Germany) and was processed within two hours after taking the blood. All blood samples were obtained with the agreement of the patients in accordance with institute guidelines and after IRB approval. All experiments were carried out ten times, and averages were calculated from the results. Mononuclear cells (MNCs) were separated from whole blood by Ficoll® (Biochrom Germany) and by OncoQuick® (Greiner BioOne Germany) density gradient centrifugation.

Oncoquick® Density Gradient Centrifugation

Precooled 50 ml centrifuge tubes which contained 15 ml of separation medium below a porous barrier which separates an upper and a lower compartment were charged with 10 to 30 ml of blood and centrifuged in a swing-out rotor (Hettich, Germany) at 1600 g for 20 min at 4° C. The total volume in the upper compartment, including the interphase of mononuclear cells, was poured into a fresh centrifuge tube. The porous barrier prevented any contamination of the separated MNCs with the fraction of pelleted blood cells. The cells were then centrifuged with washing buffer at 200 g for 12 minutes at 4° C., and the supernatant was aspirated off. The pelleted cells were used for further investigation.

Ficoll® Density Gradient Centrifugation 50 ml centrifuge tubes with a porous filter disk at 15 ml (Leucosep®, Greiner BioOne Germany) and containing 15 ml of Ficoll® were charged with 10 ml of blood and centrifuged at 10 000 g for 10 min at room temperature. In order to isolate the MNCs, the entire volume of the upper compartment of the Leucosep® tube was poured into a fresh 50 ml centrifuge tube. The isolated cells were washed with PBS (Boehringer, Germany) at 500 g for 15 min at 4° C. The supernatant was aspirated off and used for further detection of disseminated tumor cells. The low g values employed for the washing steps (500 g for Ficoll® and 200 g for Onco-Quick®) were chosen in order to ensure integrity of the cells for the immunocytological investigations.

Depletion of Blood Cells after Density Gradient Centrifugation

To quantify the cells separated by the two density gradient centrifugation methods, 30 ml of blood was taken from 10 tumor-free and healthy subjects and divided into three 10 ml aliquots. One aliquot was prepared with Ficoll® and one aliquot with OncoQuick® for each patient. The third aliquot remained unprocessed. The cells separated by the two centrifugation methods, and the unprocessed whole blood sample, were analyzed using the Sysmex SE-9000® (Sysmex Germany) hematology analyzer which is employed clinically for blood cell differentiation. Scattergraphs were constructed by measuring the resistance with direct current and high-frequency alternating current, thus showing the three-dimensional distribution of cell size and internal cell density.

Isolation of Tumor Cells after Density Centrifugation

In order to determine the proportion of tumor cells isolated after preparation of whole blood with Ficoll® and OncoQuick®, spiking experiments were carried out with the colorectal carcinoma cell line HT-29. 40 ml of blood was taken from each of ten tumor-free subjects and divided into four 10 ml aliquots. Two aliquots from each subject were spiked with $2.7 \times 10^6$ or $2.7 \times 10^5$ tumor cells, while the other two aliquots were not manipulated. One pair of unspiked and spiked blood samples was processed with Ficoll®, and the other pair with OncoQuick®, and investigated using the hematology analyzer. The difference in the total number of MNCs between the spiked and unspiked samples was ascribed to the spiked tumor cells. Comparison of the number of spiked tumor with this calculated number of isolated tumor cells after Ficoll® or OncoQuick® treatments served as a measure of the proportion of tumor cells isolated using the respective method.

Detection of Disseminated Tumor Cells

Tumor cells were detected by immunocytochemistry (ICC) and reverse transcriptase polymerase chain reaction (RT-PCR). In order to determine the detection rate of spiked tumor cells in blood which has been treated with either Ficoll® or OncoQuick®, 10 ml blood samples from tumor-free subjects were spiked with an increasing number of tumor cells (0, 10, 100 and 1000 tumor cells for RT-PCR detection and 100 and 1000 tumor cells for ICC detection).

Immunocytochemistry

The total number of separated MNCs with and without spiked tumor cells was determined by microscopy using a Neubauer cell chamber. A maximum of 200 000 cells was centrifuged on each cover slip. The preparations obtained by cytocentrifugation in this way were fixed with acetone at room temperature for 10 min, air-dried and then preincubated with antibody-free human serum for 25 min in order to block nonspecific antibody binding. Cytokeratin-positive cells were identified by the mouse anticytokeratin monoclonal antibody (MAb) A45-B/B3 (Micromet, Germany) which detects a common epitope on various cytokeratin proteins, including cytokeratin 8, 18 and 19, and with the monoclonal antibody CK-20 (Dako Germany) which is directed against cytokeratin 20 (CK20). After incubation with the primary antibody for 45 minutes, the reaction was developed by the alkaline phosphatase-antialkaline phosphatase (APAAP) technique. The number of cytokeratin-positive cells was determined by microscopy by two people independently of one another.

Cytokeratin 20 RT-PCR

Total RNA was isolated from the cell pellets obtained by Ficoll® or OncoQuick® treatments using the High Pure® RNA Isolation Kit (Roche, Germany). Amplification of CK-20 mRNA (Moll et al., Differentiation 1993; 53: 75-93) was carried out in a one-stage RT-PCR using the Titan One® tube RT-PCR kit (Roche, Germany). The PCR was carried out in a reaction volume of 50 µl, including not more than 29.5 µl of template RNA for OncoQuick® samples and not more than 10 µl of template RNA for Ficoll® samples, in order to avoid RNA overloading. An RT-PCR amplification carried out using a set of CK-20-specific primers described by Funaki et al., Br. J. Cancer 1998; 77: 1327-1332, for all samples in a Varius-V® thermocycler (Landgraf, Germany), as described in an earlier study (Rosenberg et al., J Clin Oncol 2002; 20: 1049-1055). Efficient amplification was obtained throughout from all samples and was checked using a β2-microglobulin RT-PCR. The PCR products were fractionated on a 2% agarose gel. The template RNA was replaced by nuclease-free water for suitable negative controls. Extracted total RNA from the colorectal carcinoma cell line HT-29 was analyzed as positive control.

Specificity of CK-20 RT-PCR in Combination with OncoQuick®

In order to determine the specificity of CK-20 RT-PCR for detecting tumor cells, blood samples from 30 tumor-free patients showing no signs of a cancer were investigated. 30 ml of blood were taken from each of 30 patients with bone fractures. The total amount of blood was divided into two halves for further density gradient centrifugation with OncoQuick® and Ficoll®. CK-20 RT-PCR was carried out after extraction of RNA from all blood samples.

In addition, 15 ml blood samples from five tumor-free patients were investigated for CK-20 expression in the cell fraction above the porous barrier and in the cell fraction below the porous barrier after OncoQuick® or Ficoll® density gradient centrifugation. The cell fractions above and below the porous barrier of the blood samples were separated after density gradient centrifugation, Total RNA was extracted and investigated by CK-20 RT-PCR and real-time CK-20 LightCycler® RT-PCR (Soong et al., Clin Cancer Res 2001; 7: 3423-3429) to quantify CK-20 expression. In addition, lysis of the erythrocytes in the cell fraction underneath the porous barrier, which contains the erythrocytes, was carried out.

Clinical Evaluation

The clinical benefits of OncoQuick® were validated by finally investigating 37 patients investigated for staging of gastrointestinal cancer. Two samples of 20 ml of peripheral blood were obtained preoperatively from each patient. All the blood samples were centrifuged with the OncoQuick® density gradient. Circulating tumor cells were detected by the cytokeratin CK-20 RT-PCR. The detection rates were compared with the presence of remote metastases and statistically analyzed by the chi-square test at a significance level of $p \leq 0.05$.

2. Results

Quantification and Characterization of the Enriched Cell Fraction

Depletion of Blood Cells after Density Gradient Centrifugation

Characterization of the various blood cell fractions from 10 ml of untreated whole blood by the hematology analyzer revealed an average cell count of $6.0 \times 10^7$ white blood corpuscles (WBC), $4.6 \times 10^{10}$ red blood corpuscles (RBC) and $2.3 \times 10^9$ blood platelets. The WBC differentiation is shown in table 1.

Table 1 shows the comparison of the cell count from the enriched interphase from 10 ml of peripheral blood from healthy subjects after enrichment with Ficoll® and after density gradient enrichment forms the depletion factor.

|  | 10 ml of blood | Ficoll ® preparation n = 10 | | OncoQuick ® preparation n = 10 | |
|---|---|---|---|---|---|
|  | n = 10 cell count | cell count | depletion | cell count | depletion |
| Red corpuscles ± SD | $4.6 \times 10^{10} \pm 3.5 \times 10^9$ | $8.0 \times 10^7 \pm 2.8 \times 10^7$ | 575-fold | $3.6 \times 10^6 \pm 1.7 \times 10^6$ | 12778-fold |
| Blood platelets + SD | $2.3 \times 10^9 \pm 8.6 \times 10^8$ | $4.1 \times 10^8 \pm 1.7 \times 10^8$ | 5.6-fold | $1.6 \times 10^6 \pm 5.2 \times 10^7$ | 14.4-fold |
| White blood corpuscles ± SD | $6.0 \times 10^7 \pm 1.6 \times 10^7$ | $1.6 \times 10^7 \pm 5.2 \times 10^6$ | 3.8-fold | $9.5 \times 10^4 \pm 1.5 \times 10^4$ | 632-fold |
| Lymphocytes + SD | $1.9 \times 10^7 \pm 1.1 \times 10^7$ | $1.1 \times 10^7 \pm 4.9 \times 10^6$ | 1.7-fold | $2.7 \times 10^4 \pm 1.7 \times 10^4$ | 704-fold |
| Monocytes ± SD | $5.0 \times 10^6 \pm 1.5 \times 10^6$ | $3.5 \times 10^6 \pm 3.4 \times 10^5$ | 1.4-fold | $1.0 \times 10^4 \pm 3.0 \times 10^3$ | 500-fold |
| Neutrophils ± SD | $3.5 \times 10^7 \pm 7.0 \times 10^6$ | $8.7 \times 10^5 \pm 4.0 \times 10^5$ | 40-fold | $5.4 \times 10^4 \pm 2.5 \times 10^4$ | 648-fold |
| Eosinophils ± SD | $9.4 \times 10^5 \pm 6.2 \times 10^5$ | $4.9 \times 10^4 \pm 8.7 \times 10^4$ | 19-fold | $2.0 \times 10^3 \pm 2.8 \times 10^3$ | 470-fold |
| Basophils ± SD | $3.2 \times 10^5 \pm 3.3 \times 10^5$ | $2.0 \times 10^5 \pm 1.8 \times 10^5$ | 1.6-fold | $4.0 \times 10^3 \pm 3.2 \times 10^3$ | 80-fold |

The interphase recovered from 10 ml of blood after Ficoll® treatment consisted of $1.6 \times 10^7$ WBC, $8.0 \times 10^7$ RBC and $4.1 \times 10^8$ blood platelets. The collected interphase after OncoQuick® treatment of 10 ml of blood consisted of $9.5 \times 10^4$ WBC, $3.6 \times 10^6$ RBC and $1.6 \times 10^8$ blood platelets. Ficoll® centrifugation reduced the number of WBC by a factor of 4, the number of RBC by a factor of 575 and that of blood platelets by a factor of 6 compared with the untreated whole blood fractions. For comparison therewith, OncoQuick® centrifugation leads to a greater reduction in the collected cells, with a depletion factor of 632 for WBC, 12 778 for RBC and 14 for blood platelets, compared with the fractions of the untreated whole blood.

Tumor Cell Isolation after Density Centrifugation

Recovery of $2.7 \times 10^5$ and $2.7 \times 10^6$ spiked tumor cells was comparable for both centrifugation methods (range 70% to 90%) with an average of 84% for Ficoll® and 87% for OncoQuick®, analyzed using the hematology analyzer (FIG. 1).

Detection of Disseminated Tumor Cells

Immunocytochemistry

Microscopic quantification of the separated MNCs with a Neubauer cell chamber revealed an average amount of $2 \times 10^5$ cells after OncoQuick® centrifugation and $1 \times 10^7$ cells after Ficoll® centrifugation. For further ICC evaluation, a maximum cell count of $2 \times 10^5$ cells per cover slip was centrifuged. Accordingly, all MNCs separated by OncoQuick® could be centrifuged on one to two cover slips, whereas approximately 50 Cytospins were necessary to investigate all MNCs separated by Ficoll®. The average recovery rate determined by ICC in spiking experiments with 100 and 1000 tumor cells in 10 ml of whole blood was 42% (range 25-70%), irrespective of the enrichment system used. After Ficoll® centrifugation, only 1-2% of the spiked tumor cells were detected per cover slip, whereas OncoQuick® allowed detection of 25-70% of the spiked tumor cells per cover slip (FIG. 2).

On comparison of the two monoclonal antibodies to identify the tumor cells, a higher sensitivity was found for A45-B/B3 compared with CK-20 in blood. The limit of detection for ICC was determined by carrying out spiking experiments with 10 and 100 spiked tumor cells in 30 ml of blood corresponding to the RT-PCR experiments. With the monoclonal antibody A45-B/B3, in a series of five repeated experiments, one of 10 spiked tumor cells was found twice after OncoQuick® centrifugation, whereas none of 10 spiked tumor cells were identified with the monoclonal antibody CK-20 or after Ficoll® centrifugation.

Cytokeratin 20 RT-PCR

The extracted average total RNA yields were 20 µg after Ficoll® and 1 µg after OncoQuick® density gradient centrifugation of 10 ml of blood in each case. The CK-20 RT-PCR reaction used in this example was limited to a maximum amount of 2 µg of total RNA yield or not more than 30 µl of RNA extract. It was therefore possible to analyze only 10% of the RNA yield after Ficoll® treatment in a single PCR reaction, corresponding to analysis of only approximately 1 ml of whole blood. For the PCR analysis of OncoQuick® preparations it was possible to analyze approximately 50% of the resulting RNA yield in a single PCR reaction.

Serial dilutions with the colorectal cancer cell line HT-29 to check the sensitivity of CK-20 RT-PCR revealed a limit of detection of 10 spiked tumor cells in 10 ml of whole blood for Ficoll® density gradient centrifugation (FIG. 3). Consistent with the superior depletion of blood cells by OncoQuick® centrifugation and the subsequent smaller amount of blood cell RNA it was possible to increase the blood volumes to up to 30 ml for OncoQuick® preparations and RT-PCR analysis, with a limit of detection of 10 spiked tumor cells in 30 ml of blood (FIG. 3). It can be stated in summary that tumor cell RNA was obtained in a higher concentration with less contaminating blood cell RNA after blood preparation with OncoQuick® compared with Ficoll®.

Specificity of CK-20 RT-PCR after OncoQuick® Density Gradient Centrifugation

Thirty tumor-free blood samples were investigated for "false-positive" CK-20 expression based on illegitimate transcription or pseudogenes. All samples depleted by OncoQuick® centrifugation were negative in the RT-PCR for CK-20 (0%), whereas 3 of 30 samples (10%) depleted by Ficoll® centrifugation were positive, even though these patients did not have cancer.

For further investigation, the cells below and above the porous layer of 5 tumor-free blood samples were analyzed after OncoQuick® centrifugation. Whereas the mononuclear cell fraction of the interphase above the porous barrier showed no CK-20 expression in all 5 tumor-free blood samples after OncoQuick® centrifugation, the cell fraction below the porous barrier expressed CK-20 in all five samples. Investigation of 10 ml of blood spiked with 100 HT29 colon cancer cells showed CK-20 expression in the cell fraction above and below the porous barrier. Additional quantification of CK-20 expression with a quantitative Lightcycler CK-20 RT-PCR in order to determine whether an increased CK-20 expression is found in the fraction below the porous barrier after tumor cell spiking revealed an average number of CK-20 copies of 3000 to 8000 in the spiked or in the unspiked cell fraction. The interphase (the cell fraction above the porous barrier) of the tumor cell-spiked blood sample contained a CK-20 copy number of 380 000, whereas no CK-20 expression was found in the unspiked cell fraction above the porous barrier. These data show that no CK-20-expressing tumor cells are below the porous barrier after OncoQuick® centrifugation.

Clinical Use

CK-20 mRNA was found in peripheral blood in 11 of 37 patients (30%) after OncoQuick® density gradient centrifugation. 26 patients (70%) were negative in both blood samples. 6 of 22 patients (27%) with upper gastrointestinal cancer expressed CK-20 mRNA in samples of peripheral blood and patients with lower gastrointestinal cancer showed CK-20 mRNA expression in 5 of 15 patients (33%). Comparison with histo-pathological data showed that 6 of 29 patients (21%) without clinical evidence of remote metastases (pM0) showed CK-20 expression, whereas 5 of 8 patients (63%) with remote metastases (pM1) expressed CK-20 mRNA ($p<0.02$) (Table 2).

Table 2 shows the detection of CK-20 mRNA in peripheral blood of 37 patients with gastrointestinal carcinomas after purification using OncoQuick®. Tumor patients with remote metastases express substantially more CK-20 mRNA (63%) than tumor patients without signs of remote metastases (21%) ($p \leq 0.02$; chi-square test).

|  | All patients | | Remote metastases pM1 | | No metastases pM0 | |
|---|---|---|---|---|---|---|
|  | n | % | n | % | n | % |
| All patients | 37 | 100% | 8 | 22% | 29 | 78% |
| CK-20 positive | 11 | 30% | 5 | 63% | 6 | 21% |
| CK-20 negative | 26 | 70% | 3 | 37% | 23 | 79% |

EXAMPLE 3

1. Patients and Methods

Patients

The investigation group comprised 42 female patients with metastatic breast cancer who were treated between November 2000 and February 2001 in the gynecology department of the Bad Trissl Hospital. All the women were postmenopausal and received hormonal treatment, chemotherapy or chemoendocrine therapy and bisphosphonates. 13 patients had malignant bone lesions as the sole metastasis site.

Bone Marrow Aspiration and Immunocytochemistry

A standard bone marrow biopsy was performed after the declaration of consent on all 13 patients who had a malignant bone metastasis as the sole metastasis site. Puncture on both anterior superior iliac spine was performed under local anesthesia. 5 ml of bone marrow were obtained, and both samples from each patient were pooled before further processing. Mononuclear cells were isolated by density gradient centrifugation with Ficoll. The number of mononuclear cells was centrifuged by cytocentrifugation on a slide. The cytospins were fixed and then stained with the pancyokeratin monoclonal antibody A45-B/B3 (Micromet, Germany). The APAAP technique was used to visualize the antibody binding (Cordell et al., 1984, J. Histochem. Cytochem.: 32, 219-229). Five slides containing a total of $2 \times 10^6$ mononuclear cells were examined by two independent observers for each patient.

Samples of Peripheral Blood and Immunocytochemistry

In addition, 20 ml blood samples were taken from the peripheral antecubital vein of all 42 patients. These patients had signs of visceral and partial bone metastases. The blood samples from each patient were processed using an optimized density gradient system, OncoQuick (Greiner BioOne, Germany). Mononuclear cells were isolated from whole blood by OncoQuick density gradient centrifugation and centrifuged by cytocentrifugation on a slide. Epithelial cells were stained with the monoclonal antibody A45-B/B3 and the APAAP technique. Because the depletion of mononuclear cells was improved on use of OncoQuick® compared with Ficoll®, all mononuclear cells were centrifuged on an average of two slides containing up to $2 \times 10^6$ mononuclear cells, which were also examined microscopically by two independent observers.

2. Results

Cytokeratin-positive Cells in Bone Marrow and Peripheral Blood

Cytokeratin-positive cells were detected in peripheral blood of 21 patients and in bone marrow of 3 patients. The number of cells detected in peripheral blood was between 1 and more than 20 per $10^6$ cells. 1 cytokeratin-positive cell per $1 \times 10^6$ mononuclear interphase cells was found in the two positive bone marrow samples. 7 patients had negative findings in the bone marrow and peripheral blood. 3 patients were cytokeratin-positive in peripheral blood and negative in bone marrow, whereas in 2 patients cytokeratin-positive cell detections were found in bone marrow but not in peripheral blood.

Cytokeratin-positive Cells and Metastasis Site 9 of 14 patients with liver metastases, but only 5 of 16 patients with bone metastases and 3 of 7 women with pulmonary metastasis site had positive findings in the peripheral blood. These data show a significant difference in the rate of detection of cytokeratin-positive cells in peripheral blood from breast cancer patients with hepatic tumor dissemination compared with other metastatic manifestations. No clear correlation could be found between the number of cells detected and the site of the metastases.

Cytokeratin-positive Cells and Survival Rate 15 of the 42 patients investigated died within a subsequent period of 9 months. The causes of death were cancer-related in all cases. 11 of these patients had positive findings in peripheral blood. 8 of these women had liver metastases. These data show that the presence of cytokeratin-positive cells in peripheral blood is associated with the following clinical condition.

CONCLUSION

Density gradient centrifugation with OncoQuick in conjunction with immunocytochemical staining permits the identification of isolated tumor cells in peripheral blood of patients with advanced breast cancer. Earlier techniques were unable to isolate a significant amount of circulating tumor cells in peripheral blood because the tumor cells could not be sufficiently enriched. The method of the invention makes it possible to enrich tumor cells in peripheral blood to such an extent that the identification of circulating tumor cells becomes possible in combination with detection methods such as immunocytochemistry, PCR or flow cytometry.

This application claims priority to German application 10237296.9 filed Aug. 14, 2002, the entirety of which is hereby incorporated by reference.

The invention claimed is:

1. A method for detecting disseminated tumor cells that express any of cytokeratins 1-20 from a body fluid, in which non-tumor cells which express at least one of cytokeratins 1-20 are separated from tumor cells which express at least one of cytokeratin 1-20, the method comprising:
   a) enriching tumor cells by a cell separation medium which has a density in the range from 1.055 to 1.065 g/ml being overlaid with the body fluid and being centrifuged, thus separating cytokeratin-positive and cytokeratin-negative blood cells from one another, with the enriched tumor cells being present in the same fraction as the cytokeratin-negative blood cells; wherein the centrifugation is carried out in a vessel which is divided by a porous barrier, a filter, a sieve, or a flap into an upper and a lower compartment, the cell separation medium being introduced into the lower compartment, and the body fluid being put in the upper compartment, and wherein the porous barrier, the filter, the sieve or the flap has a thickness of 0.5-10 mm; and
   b) using RT-PCR with a cytokeratin 1-20 specific primer to detect said any cytokeratin 1-20 expressing tumor cells in said enriched tumor cell fraction.

2. The method of claim 1, wherein the porous barrier, the filter, the sieve or the flap has a porous size of 20-100 µm.

3. The method of claim 2, wherein the porous barrier, the filter, the sieve or the flap is a hydrophobic material or is coated with a hydrophobic material.

4. The method of claim 1, wherein the cell separation medium comprises a dye which makes the cell separation medium distinguishable in color from the overlying body fluid, and thus simplifies location of the interphase.

5. The method of claim 1, wherein in step b) there is determination in single or combination analysis of whether the enriched cells express at least one epithelial marker from cytokeratins 1-20.

6. The method of claim 1, wherein the porous barrier, the filter, the sieve or the flap has a thickness of 1-5 mm.

7. The method of claim 2, wherein the porous barrier, the filter, the sieve or the flap has a porous size of 20-30 µm.

* * * * *